United States Patent [19]

Sugimoto et al.

[11] Patent Number: 4,615,215
[45] Date of Patent: Oct. 7, 1986

[54] METHOD AND APPARATUS FOR TESTING READY-MIXED CONCRETE

[75] Inventors: Yasuhiko Sugimoto, Kyoto; Sadao Wada, Nagaokakyo; Naoyosi Tanide, Chihayaakasaka; Osamu Kawabata, Amagasaki; Tadashi Yamaguchi, Suita; Shozo Yano, Uji; Kobun Suda, Kameyama; Kazuo Nishibayashi, Yamashina; Shohei Ishida, Moriyama, all of Japan

[73] Assignees: Takenaka Komuten Co., Ltd., Osaka; Shimadzu Corporation, Kyoto, both of Japan

[21] Appl. No.: 595,249

[22] Filed: Mar. 30, 1984

[30] Foreign Application Priority Data

Apr. 20, 1983 [JP] Japan ................... 58-70798

[51] Int. Cl.$^4$ .................. G01N 33/38; G01N 5/04
[52] U.S. Cl. ......................... 73/866; 177/50; 73/61 R; 364/552
[58] Field of Search ........... 73/432 G, 432 PS, 432 R, 73/437, 61 R, 53, 863.21, 863.23, 432 Z; 364/506, 509, 552, 567, 568; 177/50

[56] References Cited

U.S. PATENT DOCUMENTS

| 3,203,591 | 8/1965 | Daulton et al. | 364/567 X |
| 3,447,906 | 6/1969 | Zimmerli | 364/567 X |
| 3,686,959 | 8/1972 | Kruiger | 73/432 PS X |
| 3,747,416 | 7/1973 | Wommack | 73/437 |
| 3,991,619 | 11/1976 | Appleford et al. | 73/437 |
| 4,196,614 | 4/1980 | McLaughlin | 73/61 R |
| 4,320,658 | 3/1982 | Hilton et al. | 73/437 |
| 4,372,405 | 2/1983 | Stuart | 73/437 X |

FOREIGN PATENT DOCUMENTS

| 816931 | 7/1969 | Canada | 73/61 R |
| 492361 | 2/1930 | Fed. Rep. of Germany | 73/437 |
| 26865 | 2/1977 | Japan | 73/437 |
| 92455 | 7/1981 | Japan | 73/432 R |
| 351157 | 9/1972 | U.S.S.R. | 73/61 R |
| 787949 | 12/1980 | U.S.S.R. | 73/437 |

OTHER PUBLICATIONS

"Proportioning Concrete by Weight the Toledo Method", published by Toledo Scale Co. in Jul. 1932; Forms 9902, 9912–9914, 9916, 9917, 9919, and 9920, cover, and testimonial letter.

Primary Examiner—Jerry W. Myracle
Assistant Examiner—Tom Noland
Attorney, Agent, or Firm—Koda and Androlia

[57] ABSTRACT

A method and an apparatus for testing the quality of ready-mixed concrete. The present invention enables the water-to-cement ratio in ready-mixed concrete to be measured quickly and precisely through the measurement of the weight and underwater weight of mortar extracted from the ready-mixed concrete whose quality is to be examined.

9 Claims, 4 Drawing Figures

METHOD AND APPARATUS FOR TESTING READY-MIXED CONCRETE

BACKGROUND OF THE INVENTION

The present invention relates to a method and an apparatus for quality investigation of ready-mixed concrete, and more particularly to a method and an apparatus for predicting the quality of hardened concrete by measuring the weight ratio of water to cement in a just-prepared concrete mixture.

Procedure for an accepting test made on ready-mixed concrete at a construction field has usually consisted of making a slump test and sampling the received ready-mixed concrete for the purpose of investigating the compressive strength after the concrete has become hardened. However, the slump test does not always give a satisfactory result in predicting the quality of hardened concrete, while the compressive strength test can not be carried out until the sampled concrete mixture becomes hardened after a predetermined period of time has passed. Therefore, the conventional acceptance test of ready-mixed concrete can not preguarantee the quality of concrete before the concrete mixture deposited at a construction field becomes hardened. Encouraged by an upsurge of quality assurance movement there have been proposed many trial methods for predicting the quality of hardened concrete from the data of unhardened concrete. However, they have a problem in the correlation to compressive strength, in rapidity and easiness of test procedure, or in economical efficiency, and hence none of them has come to be practiced or used widely.

OBJECTS AND SUMMARY OF THE INVENTION

Accordingly, the present invention is directed to avoiding the disadvantages involved in the prior art methods of concrete quality investigation, and aims at providing a method and an apparatus capable of judging the quality of concrete easily and precisely at the stage of being just mixed.

Another object of the present invention is to constitute such an apparatus so as to be used not only for an acceptance test of ready-mixed concrete received at a construction field to judge whether it has been properly compounded or not, but also for quality control of concrete mixture at a concrete mixing plant.

The present invention, which has no problems in the testing process and economical efficiency, can be used widely, and largely contributes to stabilizing the quality of concrete products.

The method and the apparatus according to the present invention have their bases on the fact that the water-to-cement ratio in ready-mixed concrete has a strong correlation with the compressive strength of hardened concrete.

According to the present invention a water-to-cement ratio in ready-mixed concrete, which ratio has a close correlation to the compressive strength of hardened concrete, can easily be measured, and accordingly, it can quickly be judged whether ready-mixed concrete has been properly compounded or not. Therefore, with the present invention applied to an acceptance test of ready-mixed concrete at a construction field, it is made possible to readjust the composition of received ready-mixed concrete, even if improperly compounded, to pre-guarantee the quality of hardened concrete at the stage of depositting the concrete mixture at a construction field. On the other hand the application of the present invention to a preparation process of concrete mixture makes it possible to lessen the scattering of the strength of hardened concrete and to stabilize the quality of concrete. As the result, in determining a mixing degree of cement in consideration of the scattering of the strength of concrete, the cement quantity to be extra added to guarantee the concrete strength not lower than a required value can be made small. Experiments have shown that the saving of cement reaches 15–30 kg for a cubic meter of concrete mixture. For the achievement of the objects and effects mentioned above, the method according to the present invention comprises sampling a given quantity of concrete mixture from ready-mixed concrete, removing the gravel component from the sampled mixture to extract the mortar component, weighing out a predetermined quantity of the mortar, measuring the underwater weight of the weighed-out mortar, and deriving the water-to-cement ratio of the ready-mixed concrete from the weight and the underwater weight of the weighed-out mortar, while the apparatus according to the present invention comprises an electronic balance with a weighing tray hanging down therefrom, a water bath capable of surrounding the weighing tray, stirring means for stirring a mortar sample placed in a sample vessel with water poured therein, means for displacing the sample vessel between the weighing tray and the stirring means, control means for controlling the electronic balance so as to weigh the weight of the mortar in the sample vessel and the underwater weight of the same, and a computer for computing the water-to-cement ratio of the mortar according to a predetermined formula with the use of the aerial mortar weight and underwater mortar weight measured by the electronic balance.

PRINCIPLE OF THE INVENTION

The present invention is based on the following principle and experimental facts.

(1) The 28-day strength $F_{28}$ of concrete is related to the cement-to-water weight ratio C/W (the inverse of the water-to-cement ratio) in prepared concrete mixture in the form of $$F_{28} = 240(C/W) - 144 \text{ (Kg/cm}^2) \tag{1}$$

where C and W are the weight of cement and that of water, respectively. The constants 240 and 144 are determined experimentally on the basis of the mixing ratio of concrete.

(2) In the process of preparing concrete mixture the weighing of cement is free from the error due to the water content contained in the object to be weighed. Therefore, an error in the cement weight measurement is equivalent to that of a weight measuring instrument, and remains within the allowable value of one percent defined in JIS A5308.

(3) Of the constituents of ready-mixed concrete, water content is largely influenced by the water contained in the sand and gravel. On the other hand a slump adjustment is made mainly by adjusting the quantity of water. Therefore, the weight ratio among the constituents are often outside the maximum allowable limit one percent defined in JIS A5308. Hence the water-to-cement ratio in usual ready-mixed concrete is influenced by the quantity of water because the cement component is kept quite exact as is mentioned above.

(4) Of four components, cement, sand, gravel and water constituting ready-mixed concrete, the gravel can easily be removed from the rest by being sifted out. Therefore, the mortar component consisting of cement, sand and water is suitable to be used as the object of examination.

As the result, the water-to-cement ratio in ready-mixed concrete can easily be determined by measuring the weight and underwater weight of the mortar sampled from ready-mixed concrete. The principle of determining the cement-to-water ratio is described in the following.

The weight M of the mortar sampled from a ready-mixed concrete is expressed by $$M = C + S + W \tag{2}$$

where C, S and W are the respective weights of the cement, the sand and the water constituting the mortar. On the other hand the underwater weight M' of the mortar is given by $$M' = M - \rho_w(C/\rho_c + S/\rho_s + W/\rho_w) \tag{3}$$

where $\rho_w$, $\rho_c$ and $\rho_s$ are the specific gravities of water, cement and sand, respectively.

From Eqs. (2) and (3)

$$W = M + C(1/\rho_s - 1/\rho_c)/(1 - 1/\rho_s) - M'/(1 - 1/\rho_s) \tag{4}$$

By introducing two constants $$k_1 = (1/\rho_s - 1/\rho_c)/(1 - 1/\rho_s)$$

and $$k_2 = 1/(1 - 1/\rho_s),$$

Eq. (4) is expressed as $$W = M + k_1 C - k_2 M' \tag{5}$$

Dividing the both sides of Eq. (5) by C gives $$W/C = M/C + k_1 - k_2 M'/C. \tag{5'}$$

If the weight ratio P of the cement in the mortar is known, $$C = M \cdot P$$

so that Eq. (5) is rewritten as $$W/C = (1 - k_2 M'/M)/P + k_1 \tag{6}$$

The water-to-cement weight ratio is thus given by Eq. (5') or (6).

DETAILED DESCRIPTION OF THE INVENTION

The method based on the present invention is described below.

The first step in this method is to sample a certain quantity of the ready-mixed concrete to be examined. The sampled ready-mixed concrete is then subjected to sifting with a sifter of 5 mm-mesh to separate the mortar component therefrom with the gravel component removed.

A predetermined weight M, for instance, 400 gr of mortar is weighed out from the above separated mortar. The weighed-out mortar, with a suitable quantity of water added thereto, is stirred to expel the air contained therein, and kept standing still, for instance, for some tens of seconds until the mortar is deposited to some extent on the bottom of the vessel. Then the underwater weight M' of the mortar is weighed with the vessel immersed in water. On the other hand a graph or a table showing the correlation between the water-to-cement ratio W/C and the underwater weight M' is prepared in advance by putting the aerial mortar weight M (=400 gr) into Eq. (6). The water-to-cement ratio in the sampled ready-mixed concrete can be obtained from the previously prepared graph or table by applying a measured value of M' thereto. The above-described embodiment of the method can be modified so as to enable the water-to-cement ratio to be obtained without preparation of the W/C-M' correlation graph or table. The water-to-cement ratio W/C has a linear correlation to the underwater weight M' if the weight M in the air is constant. Therefore, in case M is kept constant, W/C can be directly read out from the balance for weighing the underwater weight, if the division on the balance is previously calibrated against W/C according to Eq. (6). With the above embodiments employed, it takes only 6 minutes or less from sampling ready-mixed concrete to reading out its W/C.

Figure 1:
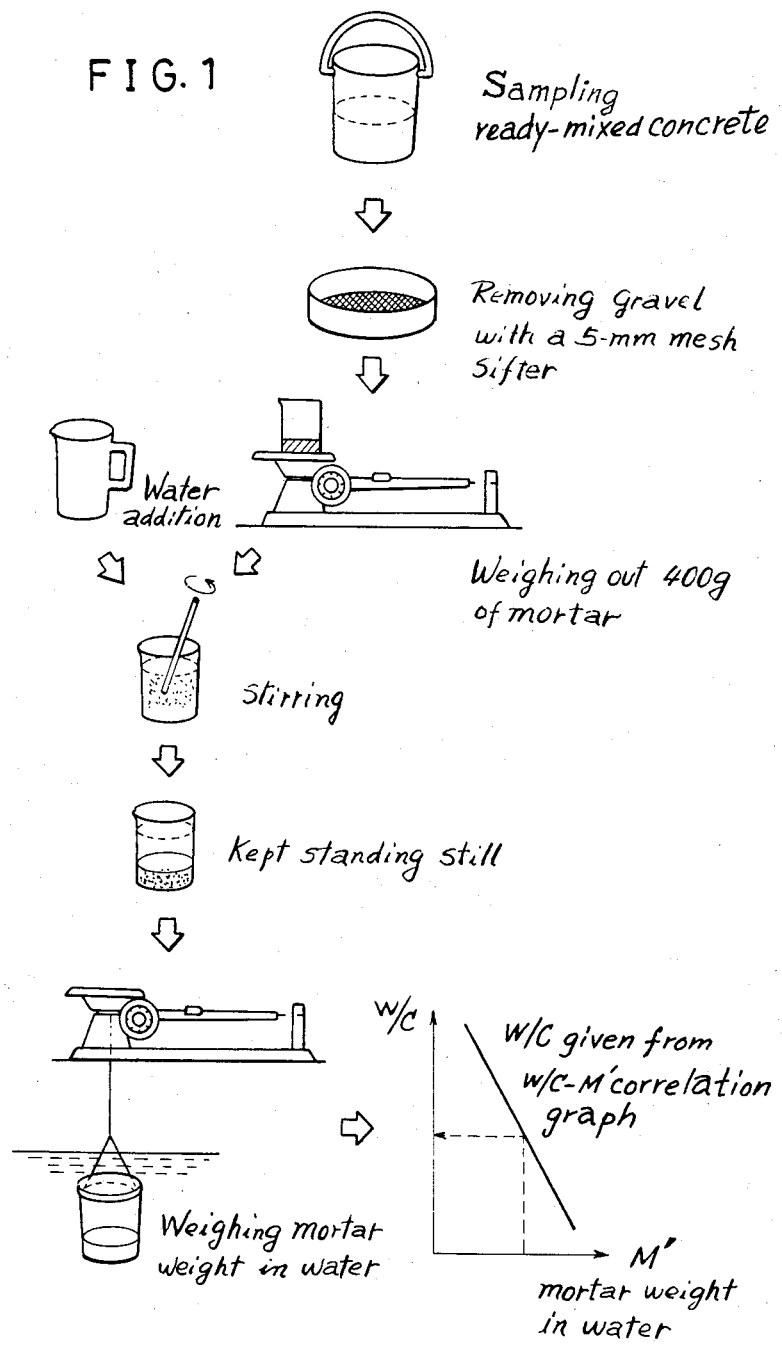
FIG. 1 shows the procedure in an embodiment of the method based on the present invention.
Figure 2:
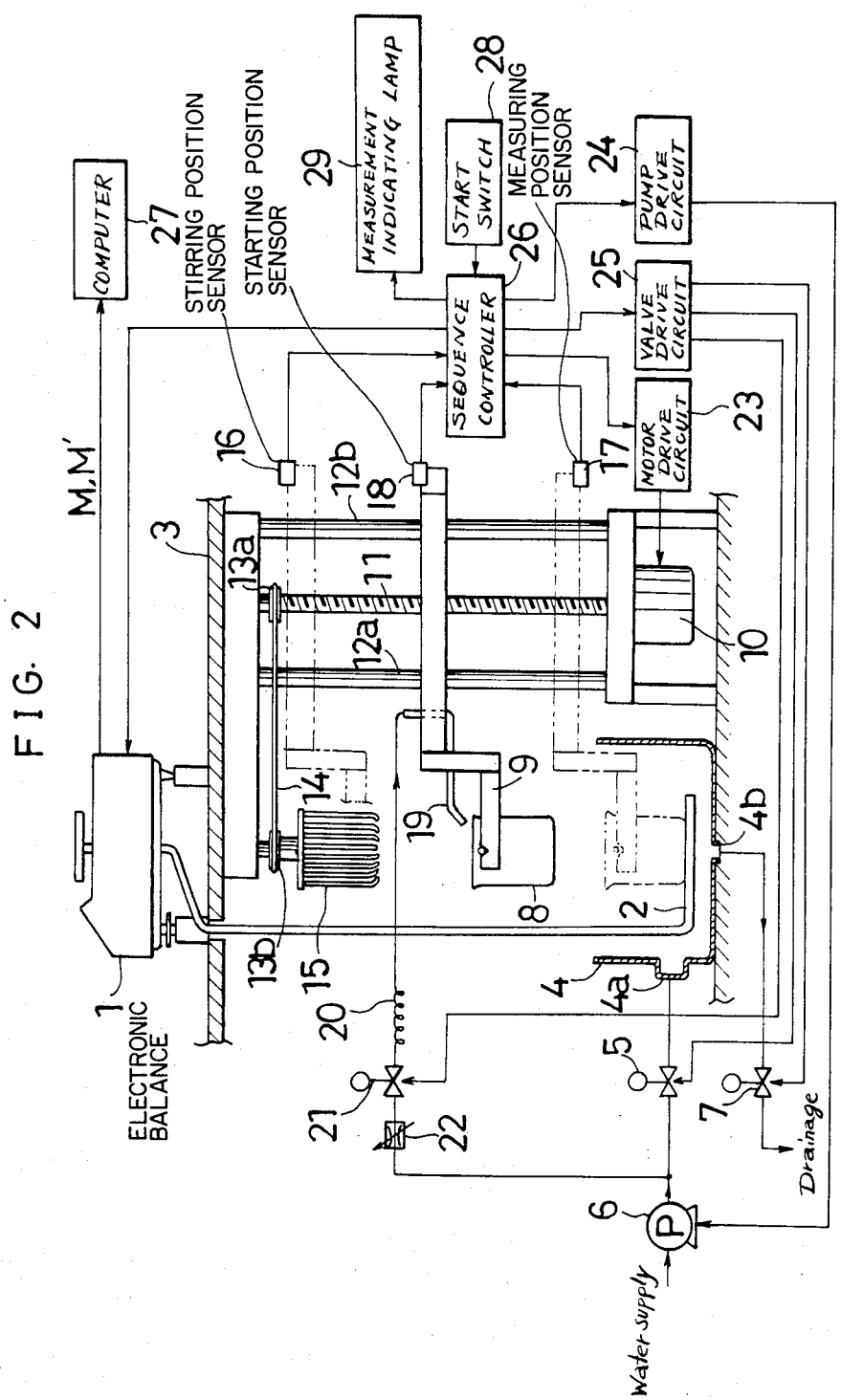
FIG. 2 shows the constitution of an embodiment of the apparatus based on the present invention.

In the following an embodiment of the apparatus based on the present invention is described with reference to FIG. 2 which shows the constitution of the embodiment. Referring to FIG. 2, an electronic balance 1, having a weighing tray 2 hanging down, is fixed on a base 3. The weighing tray 2 is positioned in a water bath 4 provided with a water supply port 4a and a draining port 4b. The water supply port 4a is connected to a water supply pump 6 through a valve 5, while the draining port is led to the atmosphere through a drain valve 7. A sample vessel 8 for containing mortar is held by a holder 9, which is engaged with a threaded bar 11 so as to be moved up and down along two guides 12a and 12b when the threaded bar 11 is rotated by a motor 10. Above the weighing tray 2 there is provided a stirrer 15 which rotates being interlocked with the threaded bar 11 through a pulleys 13a, 13b and a belt 14. The sample vessel is displaced vertically by the movement of the holder 9. With the holder 9 moved up to the uppermost position the stirrer 15 can stir the contents of the vessel 8. With the holder 9 moved down to the lowest position the vessel 8 is placed on the weighing tray 2, being made free from the holder 9. The uppermost position and lowest position are detected by a stirring position sensor 16 and a measuring position sensor 17. Midway between these two sensors 16 and 17 there is provided a starting position sensor 18 for detecting the starting position of the holder 9. With the holder 9 kept at the starting position, water can be poured into the sample vessel 8 from a nozzle 19 attached to the holder 9. The nozzle 19 is connected to the water supply pump 6 through a flexible tube 20, a water pouring valve 21 and a control valve 22. The motor 10 and the pump 6 are driven by a sequence controller 26 respectively through a motor drive circuit 23 and through a pump drive circuit 24. On the other hand the water supply valve 5, the drain valve 7 and the water pouring valve 21 are also driven by the sequence controller 26 through a valve control circuit 25. The sequence controller 26 further outputs a taring instruction signal and a weighing instruction signal to the electronic balance 1. A weight value outputted from the electronic balance 1 is inputted to a computer 27. With position signals from the stirring position sensor 16, the measuring position sensor 17 and the starting position sensor 18 being inputted to the computer 27, the computer 27 controls the apparatus according to the timing described later. The sequence controller 26 is further connected with a start switch 28 for instructing to start measuring with and a lamp (not shown) for indicating that the apparatus is being operated. Using the data inputted from the electronic balance 1, the computer 27 computes W/C according to a function previously memoried therein.

Figure 3:
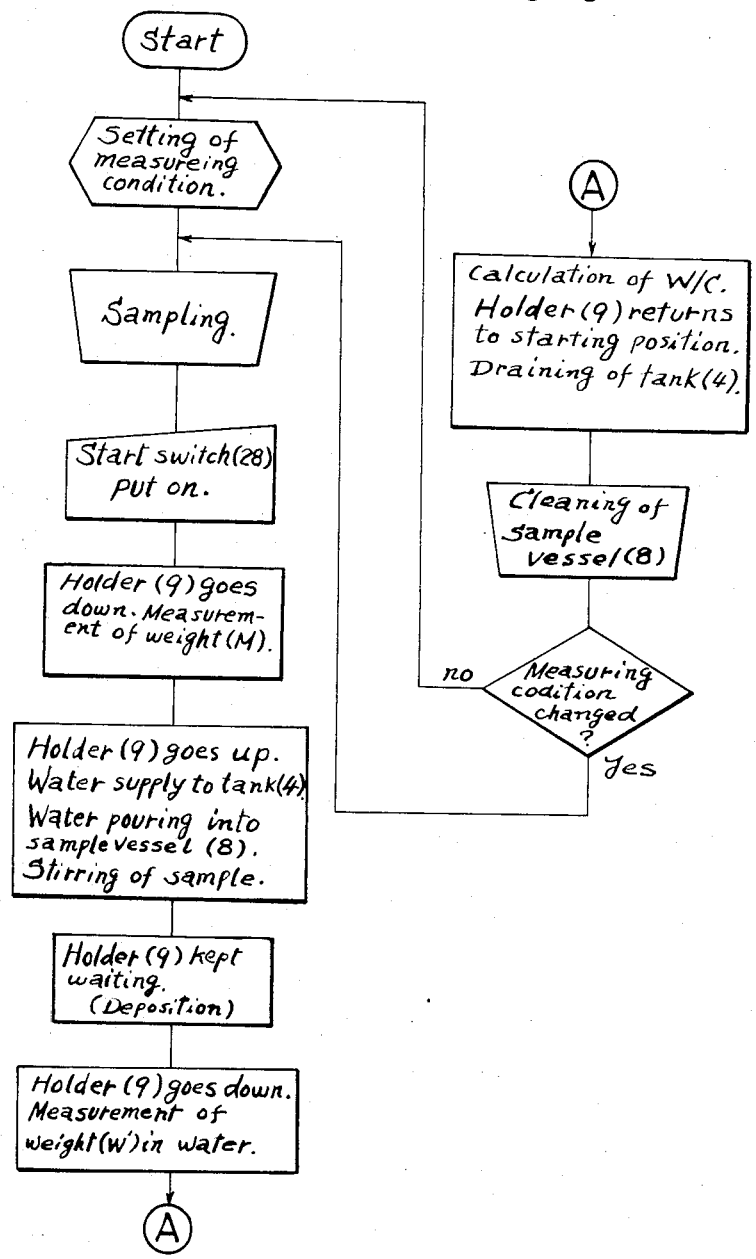
FIG. 3 is a flow-chart showing the function of the apparatus in FIG. 2.
Figure 4:
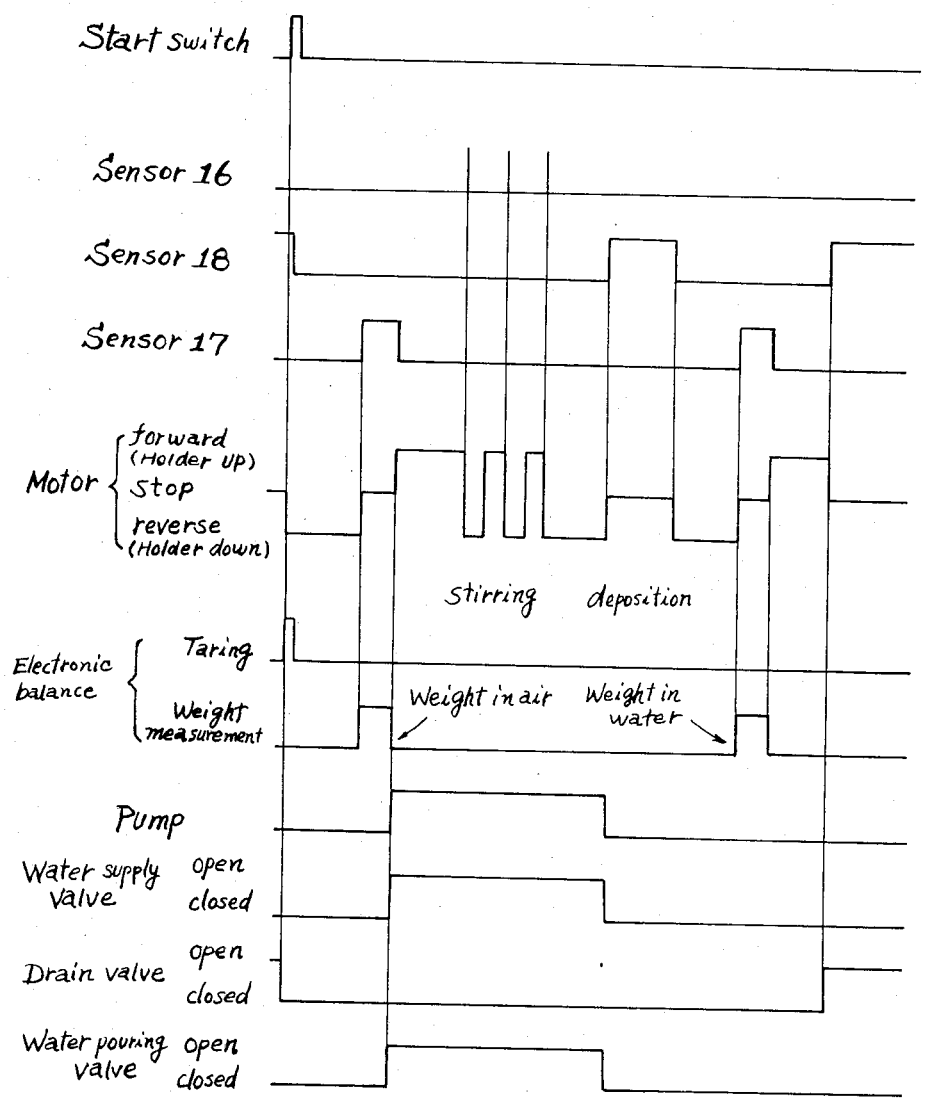
FIG. 4 is the time-chart showing the function of the apparatus in FIG. 2.

In the following the operation of the apparatus is described in detail with FIGS. 3 and 4 referred to additionally. FIG. 3 is a flow chart showing the operation of the apparatus shown in FIG. 2, while FIG. 4 shows time-charts explaining the function of the sequence controller 26 in the apparatus.

In the first place measuring conditions such as the mixing rate of cement and the specific gravities of aggregates are inputted to the computer 27. On the other hand a certain quantity of concrete mixture is sampled from ready-mixed concrete to be examined, and then sifted with a sifter of 5-mm mesh to separate mortar from the concrete mixture. An adequate weight, for instance, 400 gr of the mortar is weighed out into a sample vessel. After the sample vessel has been set at the holder 9, the sequence controller 26 is put into action with the start switch 28 turned on. The sequence controller 26 starts controlling the related elements in the apparatus in such a manner as shown with the time-charts shown in FIG. 4. With the start switch 28 turned on, a taring instruction signal is sent to the electronic balance to make it perform a taring operation. At the same time the motor 10 begins rotating in the direction to move the holder 9 downward. The rotation continues until the holder 9 stops at the measuring position which is detected by the measuring position sensor 17. After the sample vessel 8 has been placed on the weighing tray 2 with the holder 9 detached from the vessel 8, the electroniic balance measures the aerial weight M of the mortar in the vessel 8, and transmits the value to the computer 27. After the weight measurement the motor 10 again starts rotation in the direction to move the holder 9 upward. At the same time the water supply valve 5 and the water pouring valve 21 are opened and the motor 10 starts rotation to supply water both for the water bath 4 and the sample vessel 8. The water supply to the sample vessel 8 is continued over the upward movement of the holder 9 until a predetermined quantity of water is poured into the vessel 8. As soon as the holder 9 reaches the stirring position, the rotating direction of the motor 10 is reversed to lower the holder 9 again until it goes down to the starting position. This cycle of upward-and-downward movement of the holder 9 is repeated two or three times at a time interval of about three seconds. In this cyclic movement, while the holder 9 is at or near the stirring position, the stirrer 15 stirs the water-added mortar in the sample vessel 8 to expel the air contained in the mortar. After the stirring operation has been finished, the holder 9 is kept remaining still at the starting position for 10 to 20 minutes for making the mortar deposit at the bottom of the vessel 8 to some extent. While the holder 9 is kept remaining at the starting position, the motor 10 stops and the valves 5 and 21 are closed. At the next step the holder 9 is lowered to the measuring position to place the sample vessel 8 on the weighing tray 2 to make the electronic balance 1 measure the underwater weight M' of the mortar. The measured value of M' being transmitted from the electronic balance 1 to the computer 27, which computes the water-to-cement weight ratio W/C from the previously stored aerial weight M and the underwater weight M' according to Eq. (5') or (6) previously memories in the computer 27. After the measurement of W/C, the holder 9 returns to the starting position and waits for the next operation of measurement. According to the apparatus based on the present invention, it takes only about 2 minutes and 30 seconds from turning on the start switch 28 to obtaining the water-to-cement ratio W/C.

Further the method or the apparatus according to the present invention can be applied to the procedure for an emergency correction of concrete composition at a construction field, because the quality of a concrete mixture can be examined very rapidly according to the present invention. The conventional method of correction of concrete composition is to bring a tested slump magnitude and a measured air quantity close to expected values. However, such a method can not achieve a proper correction of the concrete quality. Although a slump adjustment itself can be executed by adjusting the quantity of water, the magnitude of slump is influenced not only by the quantity of water but also by the particle size of aggregates, mixing temperature, actual volume ratio and the quantity of air. Therefore, if the slump magnitude is adjusted only by adjusting the quantity of water, a change in the water-to-cement ratio may affect the compressive strength of hardened concrete.

By applying the method and the apparatus based on the present invention to the procedure for an emergency correction of concrete composition together with a slump test and an air quantity measurement, the water-to-cement ratio W/C in ready-mixed concrete can quickly be measured so that it can be made possible to keep not only the quantities of slump and air but also the water-to-cement ratio within stipulated values without deteriorating the compressive strength of hardened concrete. As is mentioned previously, the quantity of cement per $m^3$ of concrete is nearly equal to a stipulated value in usual ready-mixed concrete. It is, therefore, possible to adjust the magnitude of slump, the quantity of air and the water-to-cement ratio simultaneously by correcting the coposition of ready-mixed concrete according to the table given below. The table is prepared on the basis of the theory of concrete mixing, the RC instructions of the Society of Civil Engineering and other various experimental results.

| Deviation from the stipulated value | Correction of fine aggregate | Correction of water quantity (kg/m³) of concrete |
|---|---|---|
| For every one unit (1 cm) increase (decrease) of slump | No correction | To increase (decrease) by 1.2% |
| For every one unit (1%) increase (decrease) of air | To increase (decrease) by 0.7% | To increase (decrease) by 3% |
| For every one unit (5%) increase of W/C | To decrease (increase) by 1.0% | No correction |

The correction of aggregate ratio and the correction of water quantity per m³ of concrete shown in the above table, and the correction of cement quantity per m³ of concrete due to these corrections are expressed by the following formulae:

$$\Delta W = -\{(SL - SL_o)\alpha - (A - A_o)\beta\}CW/C \quad (7)$$

$$\Delta S/a = (A - A_o)\gamma - (W/C - W_o/C)\delta \quad (8)$$

$$\Delta C = \frac{CW/C + W}{W_o/C} - C \quad (9)$$

In the above formulae,

ΔW: Correction of water quantity per m³ of concrete (kg/m³)

ΔS/a: Correction of aggregate ratio (%)

ΔC: Correction of cement quantity per m³ of concrete (kg/m³)

SL: Measured value of slump (cm)

A: Measured quantity of air (%)

$A_0$: Stipulated slump (cm)

W/C: Measured water-to-cement ratio (%)

C: Cement quantity per m³ of concrete (kg/m³)

$W_o/C$: Stipulated water-to-cement ratio (%)

α,β,γ,δ: Constants. At present 0.012. 0.03, 0.7, 20 are the best-fit on the basis of the table. Changable according to experimental results.

By applying to Eqs. (7), (8) and (9) a slump magnitude, an air quantity A and a water-to-cement ratio W/C measured on the ready-mixed concrete received at a construction field, proper correction values can quickly be obtained to readjust the composition of the ready-mixed concrete before it is deposited. Further the present invention can be applied to the process of ready-mixed concrete production to stabilize the quality of concrete. It is also possible to make a microcomputer compute and output the above correction value, with Eqs. (7), (8) and (9) previously memoried in the microcomputer.

We claim:

1. An apparatus for testing the quality of ready-mixed concrete, said apparatus comprising:

an electronic balance having a weighing tray hanging down therefrom;

a water bath for immersing said weighing tray in water;

water supply means for supplying water to said water bath;

a sample vessel in which a mortar sample is to be placed, said mortar sample being sampled from ready-mixed concrete whose quality is to be tested;

water pouring means for pouring water into said sample vessel;

stirring means for stirring the contents of said sample vessel with water poured therein;

driving means for displacing said sample vessel between said weighing tray and the position of said stirring means through a starting position where said sample vessel is made to be engaged with and detached from said driving means, said starting position being located midway between said weighing tray and said stirring means;

control means for controlling said electronic balance, said water supply means, said water pouring means, and said driving means so that said sample vessel may be firstly placed on said weighing tray to have the area weight of the contents measured, secondly brought to the position of the stirring means to have the contents stirred with water poured therein, thirdly kept standing still at said starting position for a predetermined period of time, and fourthly placed on said weighing tray to have the underwater weight of the contents measured with water supplied into said bath; and computing means for computing the water-to-cement ratio in said ready-mixed concrete according a correlation between the aerial weight and the underwater weight of said mortar sample.

2. A method for testing the quality of ready-mixed concrete, said method comprising:

separating mortar by removing gravel from said ready-mixed concrete;

sampling any adequate quantity of mortar from said separated mortar and weighing said sampled mortar;

weighing the underwater weight of said sampled mortar;

calculating the weight of the cement contained in said sampled mortar according to a cement mixing ratio in said ready-mixed concrete, said cement mixing ratio being a weight ratio of the cement to the constituents of said ready-mixed concrete, which ratio is predetermined in the process of preparing said ready-mixed concrete; and deriving the water-to-cement ratio in said ready-mixed concrete from the weight and the underwater weight of the sampled mortar, said water-to-cement ratio W/C in said ready-mixed concrete being derived in accordance with a first formula, $M/C + k_1 - k_2 M'/C$, where M and M' are respectively the weight and the underwater weight of said sampled mortar, C is the weight of the cement contained in said sampled mortar, and $k_1$ and $k_2$ are respectively $(1/p_s - 1/p)/(1 - 1/p_s)$ and $1/(1 - 1/p)$, $p_s$ and $p_c$ being respectively the known specific gravity of the sand and that of the cement, both contained in said sampled mortar.

3. A method defined in claim 2, wherein the water-to-cement ratio in said ready-mixed concrete is obtained from a table made to represent said first formula.

4. A method for testing the quality of ready-mixed concrete, said method comprising:

separating mortar by removing gravel from said ready-mixed concrete;

sampling any adequate quantity of mortar by weighing out a predetermined weight of mortar from said separated mortar;

weighing the underwater weight of said sampled mortar;

calculating the weight of the cement contained in said sampled mortar according to a cement mixing ratio in said ready-mixed concrete, said cement mixing ratio being a weight ratio of the cement to the constituents of said ready-mixed concrete, which ratio is predetermined in the process of preparing said ready-mixed concrete; and deriving the water-to-cement ratio in said ready-mixed concrete from the weight and the underwater weight of the sampled mortar, said water-to-cement ratio in said ready-mixed concrete being derived in accordance with a first formula, $$M/C + k_1 - k_2 M'/C,$$

where M and M' are respectively the weight and the underwater weight of said sampled mortar, C is the weight of the cement contained in said sampled mortar, and $k_1$ and $k_2$ are respectively $(1/p_s - 1/p)/(1 - 1/p)$ and $1/(1 - 1/p)$, $p_s$ and $p_c$ being respectively the known specific gravity of the sand and that of the cement, both contained in said sampled mortar.

5. A method defined in claim 4, wherein the water-to-cement ratio in said ready-mixed concrete is obtained from a table made to represent said first formula.

6. A method for testing the quality of ready-mixed concrete, said method comprising:

separating mortar by removing gravel from said ready-mixed concrete;

sampling any adequate quantity of mortar from said separated mortar and weighing said sampled mortar;

weighing the underwater weight of said sampled mortar;

calculating the weight of the cement contained in said sampled mortar according to a cement mixing ratio in said ready-mixed concrete, said cement mixing ratio being a weight ratio of the cement to the constituents of said ready-mixed concrete, which ratio is predetermined in the process of preparing said ready-mixed concrete; and deriving the water-to-cement ratio in said ready-mixed concrete from the weight and the underwater weight of the sampled mortar, said water-to-cement ratio W/C in said ready-mixed concrete being derived in accordance with a second formula, $$(1 - k_2 M'/M)P + k_1,$$

where M and M' are respectively the weight and the underwater weight of said sampled mortar, P is the weight ratio of mortar to cement in said sampled mortar, and $k_1$ and $k_2$ being respectively $(1/p_s - 1/p_c)/(1 - 1/p_s)$ and $(1/(1 - 1/p_s)$, $p_s$ and $p_c$ being respectively the known specific gravity of the sand and that of the cement, both contained in said sampled mortar.

7. A method defined in claim 6, wherein the water-to-cement ratio in said ready-mixed concrete is obtained from a table made to represent said second formula.

8. A method for testing the quality of ready-mixed concrete, said method comprising:

separating mortar by removing gravel from said ready-mixed concrete;

sampling any adequate quantity of mortar by weighing out a predetermined amount of mortar from said separated mortar;

weighing the underwater weight of said sampled mortar;

calculating the weight of the cement contained in said sampled mortar according to a cement mixing ratio in said ready-mixed concrete, said cement mixing ratio being a weight ratio of the cement to the constituents of said ready-mixed concrete, which ratio is predetermined in the process of preparing said ready-mixed concrete; and deriving the water-to-cement ratio in said ready-mixed concrete from the weight and the underwater weight of the sampled mortar, said water-to-cement ratio W/C in said ready-mixed concrete being derived in accordance with a second formula, $$(1 - k_2 M'/M)/P + k_1,$$

where M and M' are respectively the weight and the underwater weight of said sampled mortar, P is the weight ratio of mortar to cement in said sampled mortar, and $k_1$ and $k_2$ being respectively $(1/p - 1/p_c)/(1 - 1/p_s)$ and $1/(1 - 1/p_s)$, $p_s$ and $p_c$ being respectively the known specific gravity of the sand and that of the cement, both contained in said sampled mortar.

9. A method defined in claim 8, wherein the water-to-cement ration in said ready-mixed concrete is obtained from a table made to represent said second formula.

* * * * *